United States Patent
Steck et al.

(10) Patent No.: US 7,901,376 B2
(45) Date of Patent: Mar. 8, 2011

(54) DIALYSIS CASSETTE HAVING MULTIPLE OUTLET VALVE

(75) Inventors: John Edward Steck, Round Lake, IL (US); Douglas Reitz, Green Oaks, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 624 days.

(21) Appl. No.: 11/773,654

(22) Filed: Jul. 5, 2007

(65) Prior Publication Data

US 2009/0012460 A1    Jan. 8, 2009

(51) Int. Cl.
*A61M 37/00* (2006.01)
(52) U.S. Cl. .......................... 604/131; 604/29
(58) Field of Classification Search ............... 604/29, 604/131, 153; 417/477.2
See application file for complete search history.

(56) References Cited

U.S. PATENT DOCUMENTS

| | | |
|---|---|---|
| 329,773 A | 11/1885 | Perry |
| 2,886,281 A | 5/1959 | Canalizo |
| 3,083,943 A | 4/1963 | Stewart, Jr. et al. |
| 3,556,465 A | 1/1971 | Little |
| 3,656,879 A | 4/1972 | DeVries, Jr. |
| 3,689,025 A | 9/1972 | Kiser |
| 3,689,204 A | 9/1972 | Prisk |
| 3,709,222 A | 1/1973 | DeVries |
| 3,823,724 A | 7/1974 | Davis |
| 3,882,899 A | 5/1975 | Ginsberg et al. |
| 4,086,653 A | 4/1978 | Gernes |
| 4,096,859 A | 6/1978 | Agarwal et al. |
| 4,158,530 A | 6/1979 | Bernstein |
| 4,199,307 A | 4/1980 | Jassawalla |
| 4,236,880 A | 12/1980 | Archibald |
| 4,240,408 A | 12/1980 | Schael |
| 4,252,115 A | 2/1981 | Schael |
| 4,265,601 A | 5/1981 | Mandroian |
| 4,273,121 A | 6/1981 | Jassawalla |

(Continued)

FOREIGN PATENT DOCUMENTS

DE    1766588    8/1971

(Continued)

OTHER PUBLICATIONS

International Search Report and Written Opinion for International Application No. PCT/US2008/068974 mailed on Apr. 24, 2009.

*Primary Examiner* — Kevin C Sirmons
*Assistant Examiner* — Deanna K Hall
(74) *Attorney, Agent, or Firm* — K&L Gates LLP (57) ABSTRACT

A disposable pumping cassette in one embodiment includes a pump chamber; and a valve chamber in communication with the pump chamber, the valve chamber including an inlet and first and second outlets. A disposable pumping cassette in another embodiment includes a first valve chamber including an inlet and first and second outlets; and a second valve chamber including an inlet and an outlet, the second valve chamber openable to allow dialysis fluid to flow through one of the first and second outlets of the first valve chamber, through the outlet of the second valve chamber. A disposable pumping cassette in a further embodiment includes a valve chamber including a fluid inlet and first and second fluid outlets; and a flexible sheet openable to open and close only one of the first and second outlets.

20 Claims, 10 Drawing Sheets

U.S. PATENT DOCUMENTS

| | | | |
|---|---|---|---|
| 4,277,226 A | 7/1981 | Archibald | |
| 4,366,061 A | 12/1982 | Papanek et al. | |
| 4,381,003 A | 4/1983 | Buoncristiani | |
| 4,397,643 A | 8/1983 | Rygiel | |
| 4,413,988 A | 11/1983 | Handt et al. | |
| D271,801 S | 12/1983 | Preussner | |
| D271,802 S | 12/1983 | Preussner | |
| 4,468,222 A | 8/1984 | Lundquist | |
| 4,479,760 A | 10/1984 | Bilstad et al. | |
| 4,479,761 A | 10/1984 | Bilstad et al. | |
| 4,479,762 A | 10/1984 | Bilstad et al. | |
| 4,532,414 A | 7/1985 | Shah et al. | |
| 4,552,552 A | 11/1985 | Polaschegg et al. | |
| 4,558,715 A | 12/1985 | Walton et al. | |
| 4,559,036 A | 12/1985 | Wunsch | |
| 4,560,472 A | 12/1985 | Granzow et al. | |
| 4,573,992 A | 3/1986 | Marx | |
| 4,586,920 A | 5/1986 | Peabody | |
| 4,597,412 A | 7/1986 | Stark | |
| 4,613,327 A | 9/1986 | Tegrarian et al. | |
| 4,617,115 A | 10/1986 | Vantard | |
| 4,634,430 A | 1/1987 | Polaschegg | |
| 4,666,598 A | 5/1987 | Heath et al. | |
| 4,676,467 A | 6/1987 | Palsulich | |
| 4,696,671 A | 9/1987 | Epstein et al. | |
| 4,703,913 A | 11/1987 | Hunkapiller | |
| 4,711,845 A | 12/1987 | Gelfand et al. | |
| 4,718,890 A | 1/1988 | Peabody | |
| 4,747,822 A | 5/1988 | Peabody | |
| 4,770,787 A | 9/1988 | Heath et al. | |
| 4,778,451 A | 10/1988 | Kamen | |
| 4,798,090 A | 1/1989 | Heath et al. | |
| 5,062,774 A | 11/1991 | Kramer et al. | |
| 5,245,693 A | 9/1993 | Ford et al. | |
| 5,364,385 A | 11/1994 | Harms et al. | |
| 5,381,510 A | 1/1995 | Ford et al. | |
| 5,542,919 A | 8/1996 | Simon et al. | |
| 5,607,082 A | 3/1997 | Cracauer | |
| 5,609,572 A | 3/1997 | Lang | |
| 5,628,908 A | 5/1997 | Kamen et al. | |
| 5,634,896 A | 6/1997 | Bryant et al. | |
| 5,836,908 A | 11/1998 | Beden et al. | |
| 5,858,015 A | 1/1999 | Fini | |
| 5,938,634 A | 8/1999 | Packard | |
| 5,989,423 A | 11/1999 | Kamen et al. | |
| 6,129,699 A | 10/2000 | Haight et al. | |
| 6,234,538 B1 | 5/2001 | Lauer | |
| 6,234,992 B1 | 5/2001 | Haight et al. | |
| 6,270,673 B1 | 8/2001 | Belt et al. | |
| 6,321,597 B1 | 11/2001 | Demers et al. | |
| 6,382,923 B1 | 5/2002 | Gray | |
| 6,416,293 B1 * | 7/2002 | Bouchard et al. | 417/53 |
| 6,481,980 B1 | 11/2002 | Vandlik et al. | |
| 6,485,263 B1 | 11/2002 | Bryant et al. | |
| 6,491,656 B1 | 12/2002 | Morris | |
| 6,503,062 B1 | 1/2003 | Gray et al. | |
| 6,531,061 B1 | 3/2003 | Cholewa | |
| 6,579,253 B1 | 6/2003 | Burbank et al. | |
| 6,595,948 B2 | 7/2003 | Suzuki et al. | |
| 6,604,908 B1 | 8/2003 | Bryant et al. | |
| 6,638,478 B1 | 10/2003 | Treu et al. | |
| 6,645,166 B2 | 11/2003 | Scheunert et al. | |
| 6,663,359 B2 | 12/2003 | Gray | |
| 6,682,517 B1 | 1/2004 | Ezaki et al. | |
| 6,716,004 B2 | 4/2004 | Vandlik et al. | |
| 6,723,062 B1 | 4/2004 | Westberg et al. | |
| 6,743,201 B1 | 6/2004 | Donig et al. | |
| 6,749,403 B2 | 6/2004 | Bryant et al. | |
| 6,752,172 B2 | 6/2004 | Lauer | |
| 6,759,007 B1 | 7/2004 | Westberg | |
| 6,764,761 B2 | 7/2004 | Eu et al. | |
| 6,808,369 B2 | 10/2004 | Gray et al. | |
| 6,814,547 B2 | 11/2004 | Childers et al. | |
| 6,821,432 B2 | 11/2004 | Metzner | |
| 6,846,161 B2 | 1/2005 | Kline et al. | |
| 6,905,479 B1 | 6/2005 | Bouchard et al. | |
| 6,929,751 B2 | 8/2005 | Bowman, Jr. et al. | |
| 6,939,111 B2 | 9/2005 | Huitt et al. | |
| 6,953,323 B2 | 10/2005 | Childers et al. | |
| 7,004,727 B2 | 2/2006 | Kline et al. | |
| 7,004,924 B1 | 2/2006 | Brugger et al. | |
| 7,044,432 B2 | 5/2006 | Beden et al. | |
| 7,083,719 B2 | 8/2006 | Bowman, Jr. et al. | |
| 7,087,036 B2 | 8/2006 | Busby et al. | |
| 7,104,978 B2 | 9/2006 | Hilgers et al. | |
| 7,107,837 B2 | 9/2006 | Lauman et al. | |
| 7,115,228 B2 | 10/2006 | Lundtveit et al. | |
| 7,153,286 B2 | 12/2006 | Busby et al. | |
| 7,175,606 B2 | 2/2007 | Bowman, Jr. et al. | |
| 7,214,312 B2 | 5/2007 | Brugger et al. | |
| 7,238,164 B2 | 7/2007 | Childers et al. | |
| 7,278,981 B2 | 10/2007 | Ellingboe et al. | |
| D556,909 S | 12/2007 | Reihanifam et al. | |
| D556,910 S | 12/2007 | Reihanifam et al. | |

FOREIGN PATENT DOCUMENTS

| | | |
|---|---|---|
| DE | 3115665 | 11/1982 |
| DE | 3428828 | 4/1984 |
| DE | 9417416 | 2/1995 |
| DE | 19825158 | 4/1999 |
| EP | 0097432 | 1/1984 |
| EP | 0157024 | 10/1985 |
| EP | 0206195 | 12/1986 |
| EP | 0482858 | 4/1992 |
| EP | 0687474 | 12/1995 |
| EP | 1201264 A | 5/2002 |
| FR | 2749763 | 12/1997 |
| GB | 2093800 | 10/1981 |
| WO | WO86/01115 | 2/1986 |
| WO | 2005/042065 A | 5/2005 |

* cited by examiner

DIALYSIS CASSETTE HAVING MULTIPLE OUTLET VALVE

BACKGROUND

The examples discussed below relate generally to medical fluid delivery. More particularly, the examples disclose valve apparatuses and methods for automated peritoneal dialysis ("APD").

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

One type of kidney failure therapy is peritoneal dialysis, which uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD"). CAPD is a manual dialysis treatment. Here, the patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during dialysate. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

Peritoneal dialysis systems are becoming increasingly complicated and hence requiring more valves to operate the fluid flow of the systems. A need therefore exists for an improved valve, system and method for operating same.

SUMMARY

The present disclosure pertains to a fluid valve and disposable cassette using the fluid valve. In the medical fluid delivery industry in which drugs or blood are being introduced or reintroduced into the patient, the fluid lines carrying the drugs or blood need to be sterile. In many cases, the delivery system is not complicated and can be controlled manually by for example clamping and unclamping sterilized tubing carrying the drugs or blood. In other systems, such as automated dialysis systems, the fluid delivery is rather complicated. Here, it is desirable to clamp fluid lines automatically, especially in a home treatment in which the operator is a patient or family member and/or the treatment is performed while the patient is sleeping or trying to relax.

To accommodate the relatively complex fluid delivery regimes, medical fluid delivery systems such as dialysis systems have employed disposable cassettes, which have a flexible portion that is actuatable (automatically) to pump fluid and to open and close valve chambers formed within the cassette.

It is desirable that the cassettes be small both from a manufacturing standpoint and so that the corresponding actuating instrument (e.g., dialysis machine or instrument) is likewise small. For example, it is desirable that dialysis instrument be small enough to fit in an overhead compartment of a jet airliner, so that the instrument can be carried on business or vacation. Also, welding flexible cassette sheeting to a rigid portion of the cassette becomes increasingly more difficult and expensive as the cassette size increases. At the same time, medical fluid treatments, such as dialyses treatments, are becoming more and more complicated and specialized, tending to increase the number of flowpaths and valves needed in the cassette.

The valve chamber arrangement and resulting cassette discussed herein address the cassette size/functionality problem by increasing functionality of the cassette for a given set of valve chambers. The cassette has one or more pump chamber and a plurality of valve chambers. One of the valve chambers includes an inlet and a plurality of outlets. A first of the outlets can be opened and closed selectively via a flexible sheet attached to a rigid portion of the cassette. The rigid portion defines the valve chamber wall and a protruding port within, which forms a seat for the selective opening and closing of the first outlet.

The flexible sheeting in one embodiment is sealed physically, e.g., via an ultrasonic weld or heat seal to the edges of a rigid structure of the cassette. During operation, the sheeting is pressed against the pump and valve chamber walls extending from the base wall to form sealed pump and valve chambers. In an alternative embodiment, the sheeting is additionally sealed physically to the pump and valve chamber walls, e.g., via an ultrasonic weld or heat seal to form sealed pump and valve chambers. On the opposite side of base wall, the sheeting can be sealed to the flow path forming walls extending from the base wall either mechanically or physically as just described.

The valve chambers include outlet seats, which in one embodiment are cylindrical ports extending from the base wall. In one implementation, the port is located at a center of the valve chamber, which can itself be at least substantially cylindrical. The valve chambers also include inlet apertures which reside in the base wall on one side of the outlet port, between the protrusion and the valve chamber wall. As described herein, certain ones of the valve chambers include a second outlet, which is an aperture in the base wall, residing at an opposite side of the port from the inlet aperture, between the port and the valve chamber wall.

The inlet and second outlet in one embodiment are apertures formed in a base wall of the cassette and therefore do not open and close with the flexing of the cassette sheeting. The base wall in general separates pump chamber and valve chamber side of the cassette from a flow path side of the cassette. For example, an inlet flow path leading to the valve chamber inlet and first and second outlet flow paths leading from the first and second valve chamber outlets can be located on an opposite side of the base from the valve chamber and cooperating pump chamber.

The second outlet of the dual outlet valve chamber is controlled by a valve chamber located downstream from the dual outlet valve chamber, that is, by the valve chamber whose inlet flow path is the outlet flow path from the second (pass through) outlet of the dual outlet valve chamber. As shown below, the dual outlet valve chamber can direct flow selectively in none, one or both of two flow paths.

To shut off flow from both outlets, the flexible sheeting is pushed at areas covering the outlet seat of the first outlet of the dual outlet valve chamber and the outlet seat of the valve chamber downstream from the second outlet of the dual outlet valve chamber to close the valve seats. The flexible sheeting is operated pneumatically and/or mechanically as described below.

To shut off flow from the second outlet of the dual outlet valve chamber but allow fluid to flow from the first outlet of the dual outlet valve chamber, the flexible sheeting is compressed against the outlet seat of the downstream valve chamber but pulled away from the outlet seat of the dual chamber valve. To shut off flow from the first outlet of the dual outlet valve chamber but allow fluid to flow from the second outlet of the dual outlet valve chamber, the flexible sheeting is pulled away from the outlet seat of the downstream valve chamber but compressed against the outlet seat of the dual chamber valve, e.g., pneumatically and/or mechanically. To allow flow from both outlets, the flexible sheeting is pulled away from both valve seats.

The above-described valve chamber set or arrangement is implemented in one embodiment in combination with a second valve chamber set, an intermediate valve chamber and a pump chamber having three fluid inlets. The overall configuration enables first and second medical fluids, such as, first and second dialysis fluid components (e.g., glucose and bicarbonate) to be pumped, selectively and proportionally through any one, two or three of the pump inlets.

The configuration for example enables a first fluid to be pumped through one of the pump inlets, while the second fluid is pumped through the second and third pump inlets. The configuration alternatively enables the first fluid to be pumped through two of the pump inlets, while the second fluid is pumped through the third pump inlet. The configuration further alternatively enables the first fluid to be pumped through all three pump inlets. The configuration still further alternatively enables the second fluid to be pumped selectively through all three pump inlets.

Additional features and advantages are described herein, and will be apparent from, the following Detailed Description and the figures.

DETAILED DESCRIPTION

Figure 1:
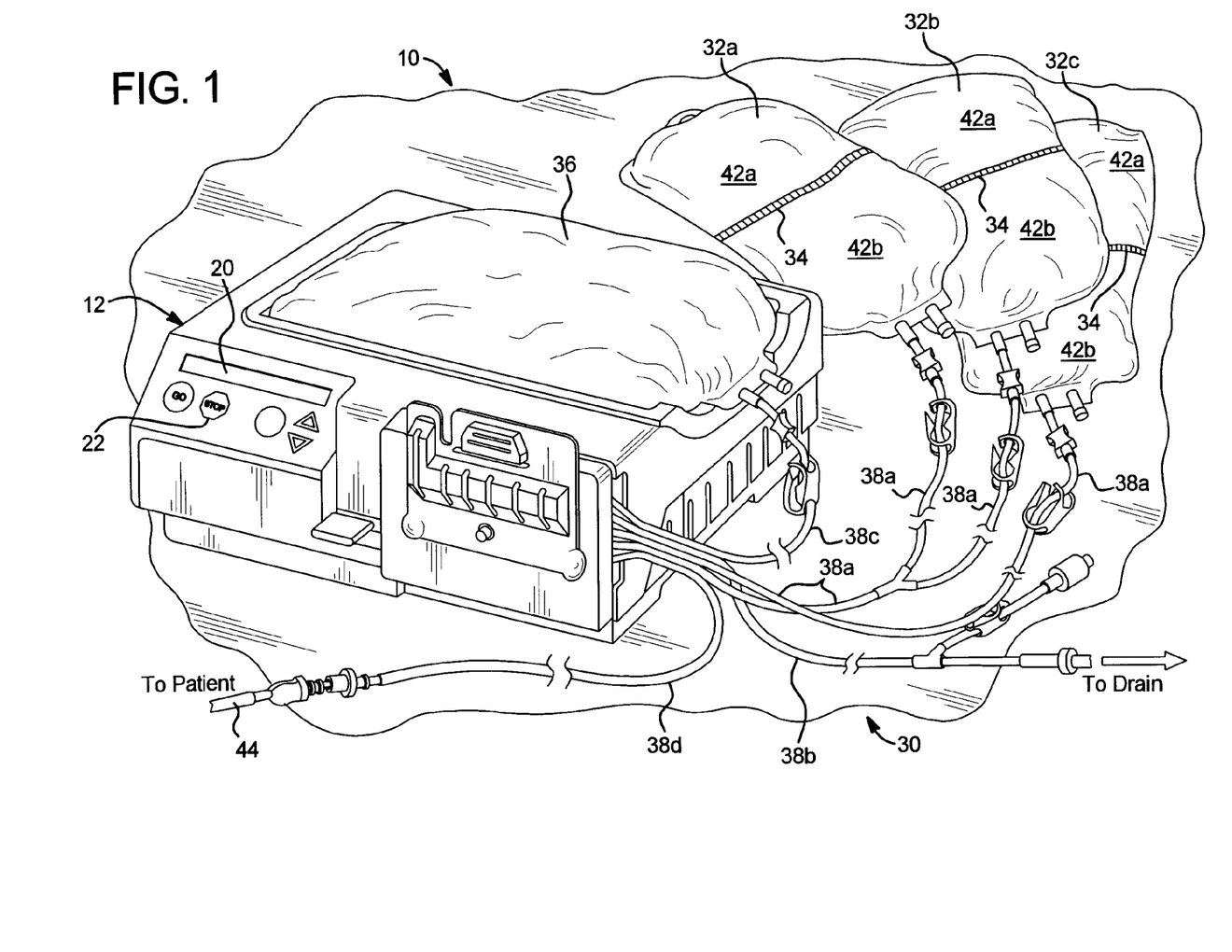
FIG. 1 is a perspective view of a medical fluid system, such as a dialysis system, which is operable with the cassette and valve configurations of the present disclosure.
Figure 2:
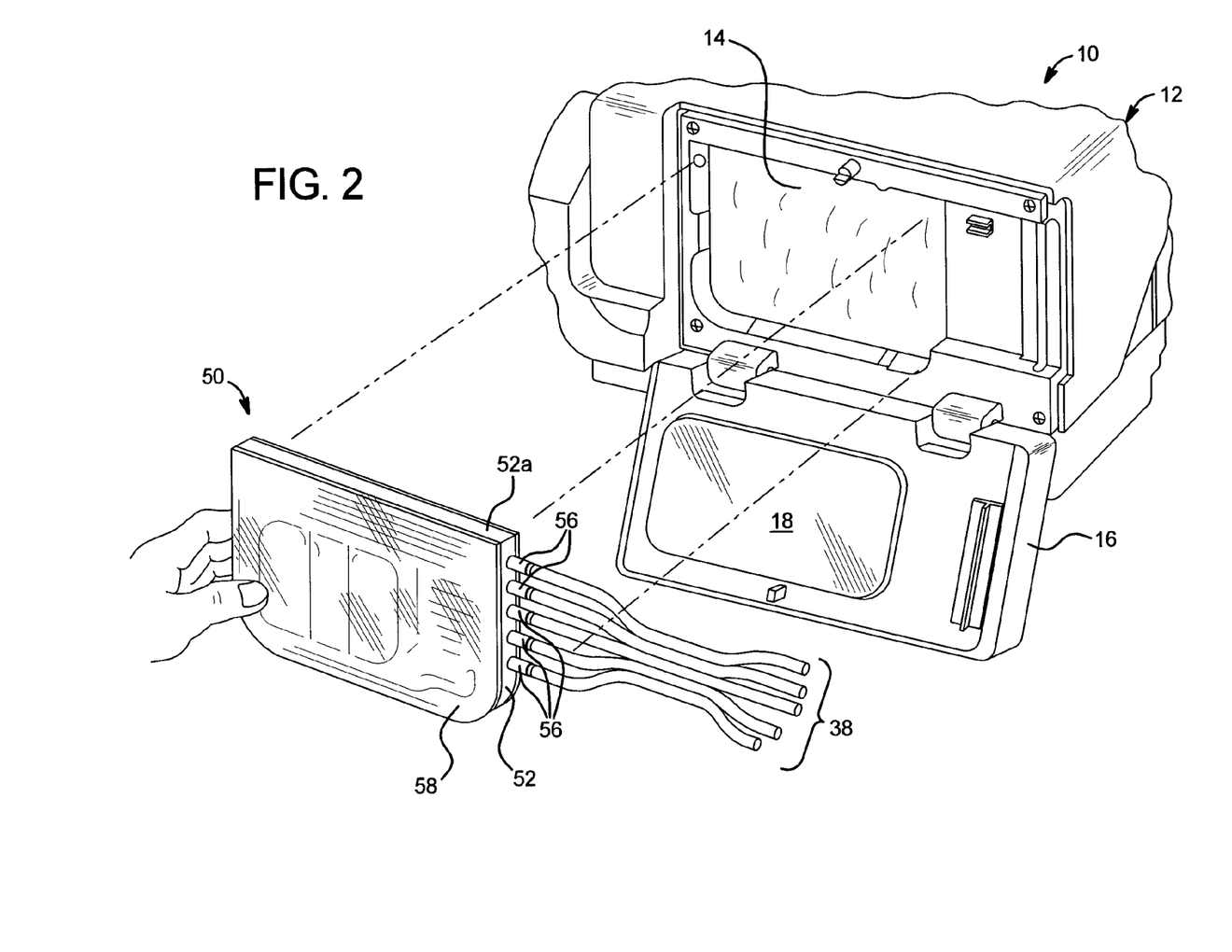
FIG. 2 is a perspective view of the system of FIG. 1 showing the cassette loading feature in more detail.

Referring now to the drawings and in particular to FIGS. 1 to 2, a renal failure therapy system 10 is provided. System 10 is applicable generally to any type of renal failure therapy system, such as peritoneal dialysis ('PD"), hemodialysis ("HD"), hemofiltration ("HF"), hemodiafiltration ("HDF") and continuous renal replacement therapy ("CRRT"). The valve configurations described below could also be used out-side of the renal field, such as for medication delivery in general, blood processing. For ease of illustration, however, system 10 is described in general as a dialysis system, and in one particularly well-suited application as a PD system.

System 10 in the illustrated embodiment includes a dialysis instrument 12. Dialysis instrument 12 is configured for whichever type of renal failure therapy system is used. Dialysis instrument 12 includes a central processing unit ("CPU") and a plurality of controllers (e.g., safety, valve, heater, pump, video, audio controllers) operable with the CPU. CPU operates with a graphical user-machine interface ("GUI"), e.g., via the video controller, which includes a video monitor 20 and one or more type of input device 22, such as a touch screen or electromechanical input device (e.g., membrane switch).

As seen in FIG. 1, dialysis instrument 12 accepts and operates with a disposable apparatus 30. Disposable apparatus 30 includes one or more supply bag 32a to 32c (referred to herein collectively as supply bags 32 or individually, generally as supply bag 32), shown here as dual-chamber supply bags separating two fluids via a peel or frangible seal 34. Disposable set 30 also includes a drain bag (not illustrated), a warmer bag 36, bag tubes 38a to 38d (referred to herein collectively as tubing or tubes 38 or individually, generally as tube 38) and a disposable pumping/valve cassette 50 (FIG. 2).

Depending on the type and structure of the renal failure therapy system 10, one or more of the items of disposable apparatus 30 may not be needed. For example, system 10 can pump spent fluid to a house drain, such as a toilet or sink, instead of to a drain bag. System 10 can also include an inline heater, in which case warmer bag 36 is not needed.

While three supply bags 32 are shown, system 10 can employ any suitable number of supply bags. Supply bags 32 are shown having multiple chambers 42a and 42b, separated by frangible seal 34, which hold different solutions depending on the type of therapy employed. For example, chambers 42a and 42b can hold buffer and glucose for PD or acetate and bicarbonate solution for HD. Supply bags 32 are alternatively single chamber bags, which hold a single premixed solution, such as premixed PD or HD dialysate.

As seen in FIGS. 1 and 2, a disposable cassette 50 connects to supply bags 32, drain bag and warmer bag 36 via tubes 38a, 38b and 38c, respectively. Tube 38d runs from cassette 50 to a patient connection 44. Cassette 50 in one embodiment includes a rigid structure having rigid outer walls 52, a base wall 54 (from which inner pump chambers, valve chambers and inner fluid pathways extend as shown below), rigid fluid ports 56 (connectable sealingly to tubing 38) and a pair of flexible membranes or sheets 58 sealed to outer rigid walls 52 and possibly additionally to inner rigid walls.

Instrument 12 can actuate the pump and valve chambers of cassette 50 pneumatically, mechanically or both. The illustrated embodiment uses pneumatic actuation. The HomeChoice® APD system marketed by the eventual assignee of the present disclosure, which could operate or be made operable with cassette 50, uses a pneumatic system described in U.S. Pat. No. 4,826,482 ("The '482 patent"), the entire contents of which are incorporated herein by reference. In the illustrated embodiment, instrument 12 includes a membrane 14, which creates different sealed areas with sheeting 58 at each of the pump and valve chambers of cassette 50. Membrane 14 moves with the sheeting 58 in those areas to either open/close a valve chamber or pump fluid through a pump chamber. An interface plate is located behind membrane 14 and forms part of each of a pair of fixed volume pump chambers in combination with the pump chambers (actually pump chamber portion) of cassette 50 discussed below.

Instrument 12 in the illustrated embodiment includes a door 16, which closes against cassette 50. Door 16 includes a press plate 18, which can be operated mechanically (e.g., via the closing of the door) and/or pneumatically (e.g., via an inflatable bladder located in the door behind the press plate). Pressing plate 18 against cassette 50 in turn presses cassette 50 against a pumping membrane 14 that cooperates with the sheeting 58 of cassette 50 to pump fluid and open and close valves.

The cassette interface plate (not seen) is located behind membrane 14. The cassette interface plate is configured to apply positive or negative pressure to the coactive membrane 14 and cassette sheeting 58 at the different valve and pump areas. For example, positive pressure is applied to membrane 14/sheeting 58 at an area of the sheeting located within the internal walls of cassette 50 defining the pump chambers to push fluid out of the pump chambers. Negative pressure is applied to membrane 14/sheeting 58 at that same area to pull fluid into the pump chambers. Positive pressure is applied to membrane 14/sheeting 58 at an area of the sheeting within the internal walls of cassette 50 defining the valve chambers to close off an outlet port of the valve chambers. Negative pressure is applied to membrane 14/sheeting 58 at that same area of cassette 50 to open an outlet of the valve chambers.

U.S. Pat. No. 6,814,547 ("the '547 patent") assigned to the assignee of the present disclosure, discloses a pumping mechanism in connection with FIGS. 17A and 17B, incorporated herein by reference, which uses a combination of pneumatic and mechanical actuation. FIGS. 15, 16A and 16B of the '547 patent, incorporated herein by reference, teach the use of mechanically actuated valves. The system could also be configured to operate with the pass-through valves of the present disclosure.

Figure 3:
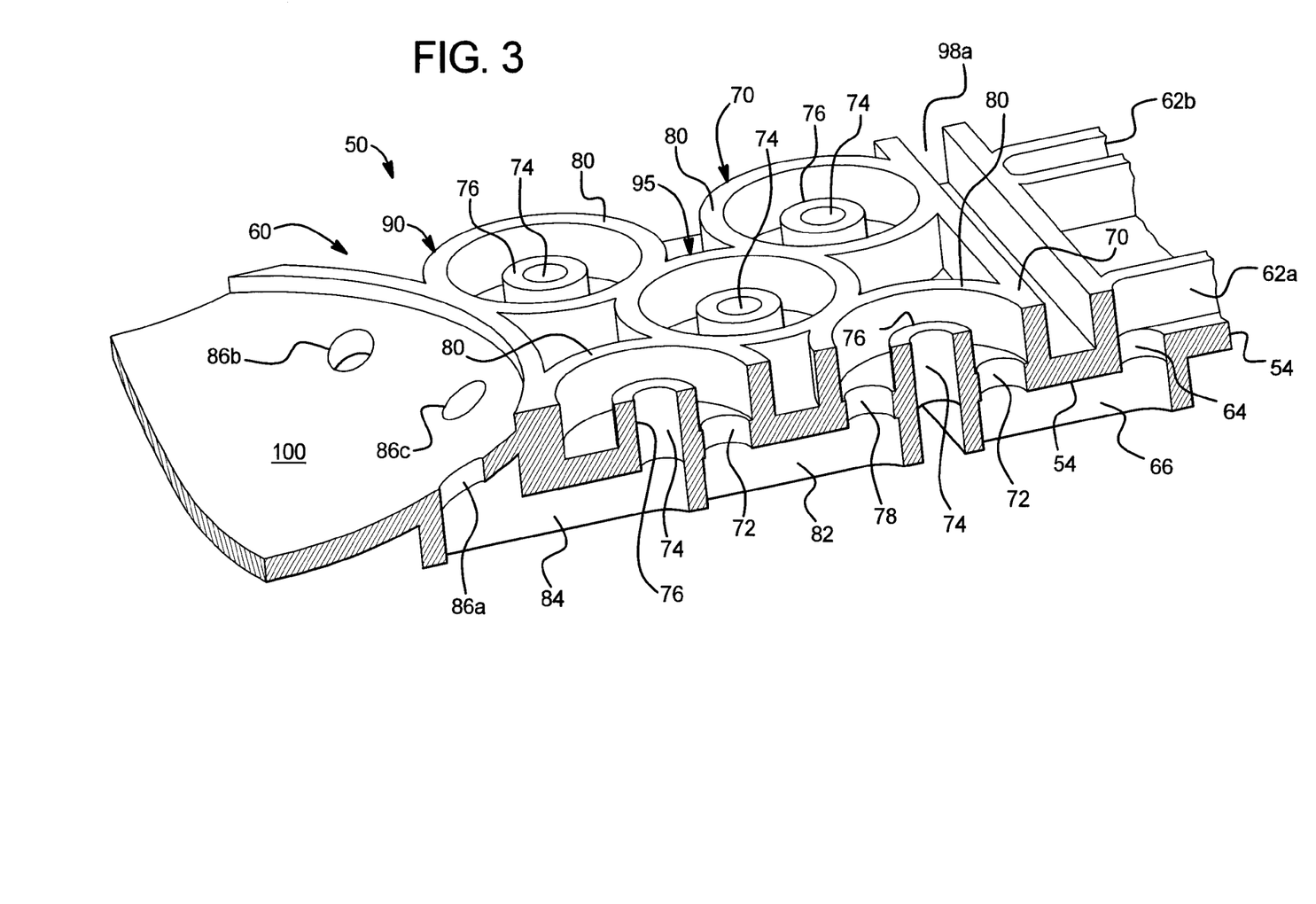
FIG. 3 is a perspective view of a cutaway portion of a disposable cassette with flexible sheeting removed to show one embodiment of the dual outlet valve chamber of the present disclosure.
Figure 4:
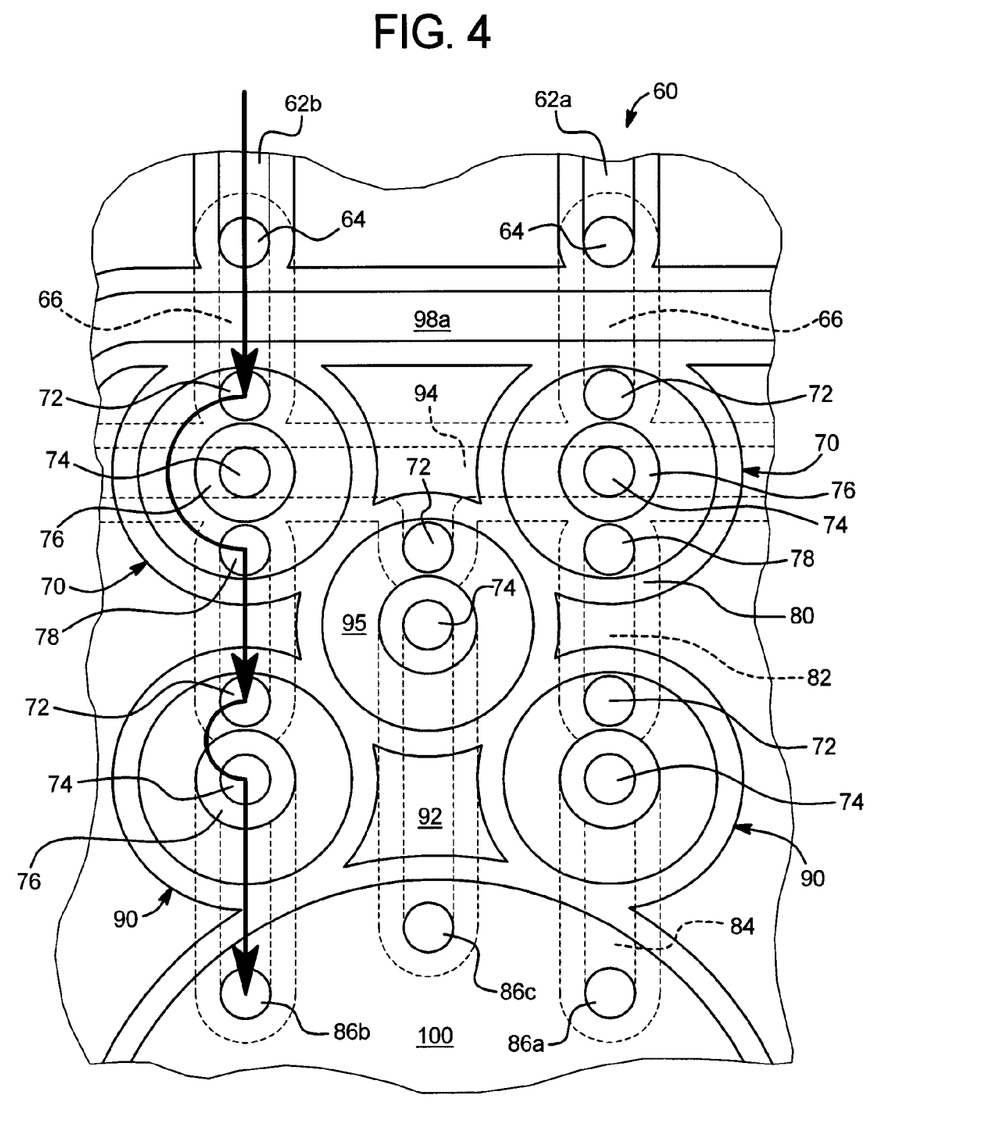
FIG. 4 is a top plan view of the cutaway portion of FIG. 3, with the cassette sheeting removed, illustrating two dual outlet valve chambers, each operating with a downstream valve, an intermediate valve between the two dual outlet valve chambers, and a pump chamber communicating with each of the valve chambers.
Figure 5:
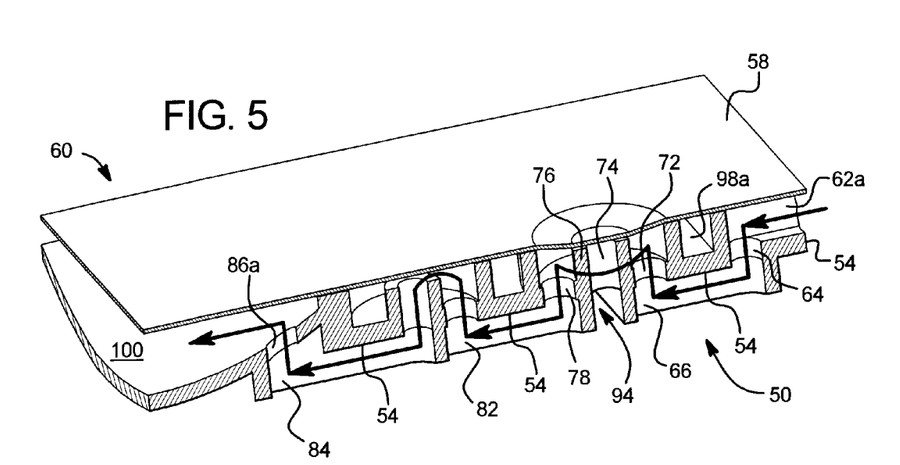
FIG. 5 is a perspective view of the cutaway portion of FIG. 3, with the cassette sheeting in place, showing a first valve state in which fluid flows from a second outlet of the dual outlet valve chamber.
Figure 6:
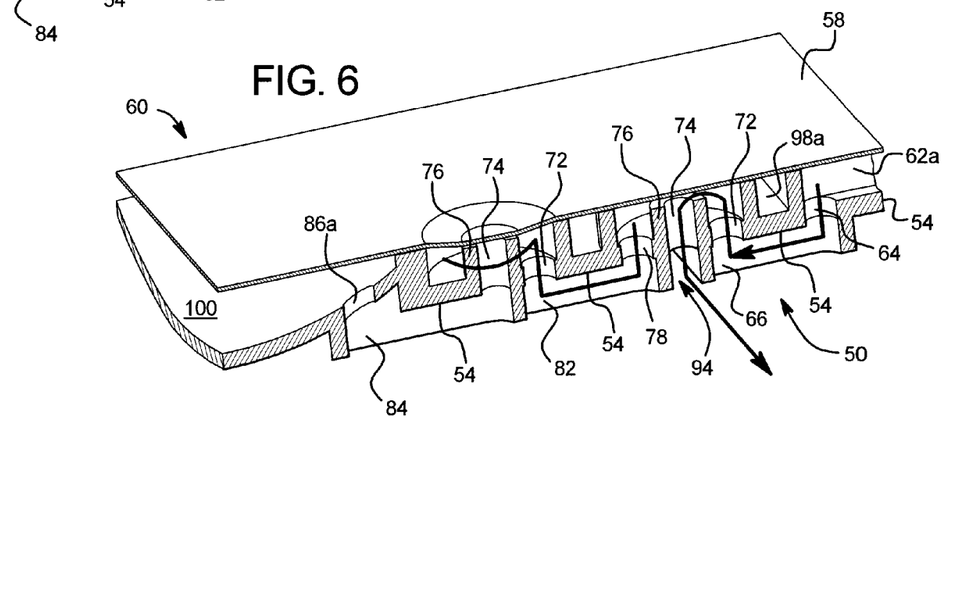
FIG. 6 is a perspective view of the cutaway portion of FIG. 3, with the cassette sheeting in place, showing a second valve state in which fluid flows from a first outlet of the dual outlet valve chamber.

Referring now to FIGS. 3 to 6, valve chamber arrangement 60, which is a section of cassette 50, illustrates one embodiment for the pass-through valves of the present disclosure, and one application for same. FIGS. 3 and 4 show valve chamber arrangement 60 with sheeting 58 removed. FIGS. 5 and 6 show valve chamber arrangement 60 with upper sheeting 58 for valve and pump chamber actuation in place.

Medical fluid, such as a dialysis fluid (e.g., premixed or a concentrate for mixing within cassette 50 or elsewhere in the disposable) enters the cassette via solution inlet fluid pathway 62a. The fluid flows from the valve/pump chamber side of cassette 50, though an aperture 64 defined in divider or base wall 54, into a second fluid pathway 66, which is located on the reverse, flow path, side of cassette 50. The fluid hence flows underneath a pathway 98a located on the valve/pump chamber side of cassette 50, which is a to-heater pathway in the illustrated example.

The fluid then flows through second fluid pathway 66 to a dual outlet valve chamber 70 of the present disclosure. Dual outlet valve chamber 70 includes an inlet 72, a first outlet 74 and a second outlet 78. First outlet 74 can be pneumatically and/or mechanically opened and closed selectively via a flexible sheet 58 that is ultrasonically bonded or heat sealed to, e.g., rigid sidewalls 52, of the cassette. First outlet 74 includes a protrusion or port 76 extending from base wall 54. Flexible sheet 58 seals to the distal end of port 76 when positive (pneumatic and/or mechanical) pressure is applied to sheet 58 at valve chamber 70 as seen in FIG. 5. Flexible sheet 58 is pulled away from the distal end of port 76 when negative (pneumatic and/or mechanical) pressure is applied to sheet 58 at valve chamber 70 as seen in FIG. 6.

Valve inlet 72 and second outlet 78 in the illustrated embodiment are apertures (e.g., circular) formed in base wall 54 of cassette 50. A wall 80, e.g., circular wall, surrounds inlet 72, first outlet 74 and second outlet 78, forming dual outlet valve chamber 70. Wall 80 extends from base wall 54 as illustrated. Wall 80 is pressed against sheet 58 and membrane 14 (described above) to form a sealed area within valve chamber 70. Alternatively, wall 80 is sealed to sheet 58 via ultrasonic weld or heat seal. Sheet 58 and membrane 14 cooperate to pneumatically open and close first outlet 74 of dual outlet valve chamber 70 as described above.

Second outlet 78 allows fluid to flow from valve chamber 70 to a downstream flow path 82, which is located on the opposite side of base wall 54 from valve chamber 70. Flow path 82 leads to an inlet 72 of a downstream valve chamber 90. Downstream valve chamber 90 includes a single inlet 72 and single outlet 74 formed via protruding port 76 as discussed above. Downstream valve chamber 90 in the illustrated embodiment does not include a second outlet 78. A wall 80, e.g., a circular wall, extends from base wall 54 and encloses inlet 72 and outlet 74. Wall 80 can be of the same size and shape as wall 80 of dual outlet valve chamber 70. Port outlet 74 can be located at the center of wall 80 for valve chambers 70 and 90 as illustrated.

Downstream chamber 90 controls second outlet 78 of the dual outlet valve chamber 70 as illustrated by FIGS. 5 and 6. In FIG. 5, flexible sheeting 58 is pushed against first outlet 74 of valve chamber 70, while the flexible sheeting is pulled away from outlet 74 of downstream valve chamber 90. This allows fluid to flow from second outlet 78 of dual outlet valve chamber 70, through downstream pathway 82, through inlet 72 of downstream valve chamber 90, out outlet 74 of valve chamber 90, through a first pump pathway 84, through a first pump opening 86a, and into a pump chamber 100 for example.

In the illustrated embodiment, pump chamber 100 includes three fluid openings 86a, 86b and 86c. Opening 86b is fed via the same valve arrangement just described for opening 86a. Opening 86b and the mirrored valve arrangement are inline with a second solution inlet fluid pathway 62b as seen in FIG. 4. Third pump opening 86c is in communication via pathway 92 with an intermediate valve chamber 95, which is located between the two dual outlet/downstream valve arrangements feeding pump chamber openings 86a and 86b, respectively. Intermediate valve chamber 95 in one embodiment is a single outlet valve chamber having the same configuration as valve chamber 90 described above.

Figure 7A:
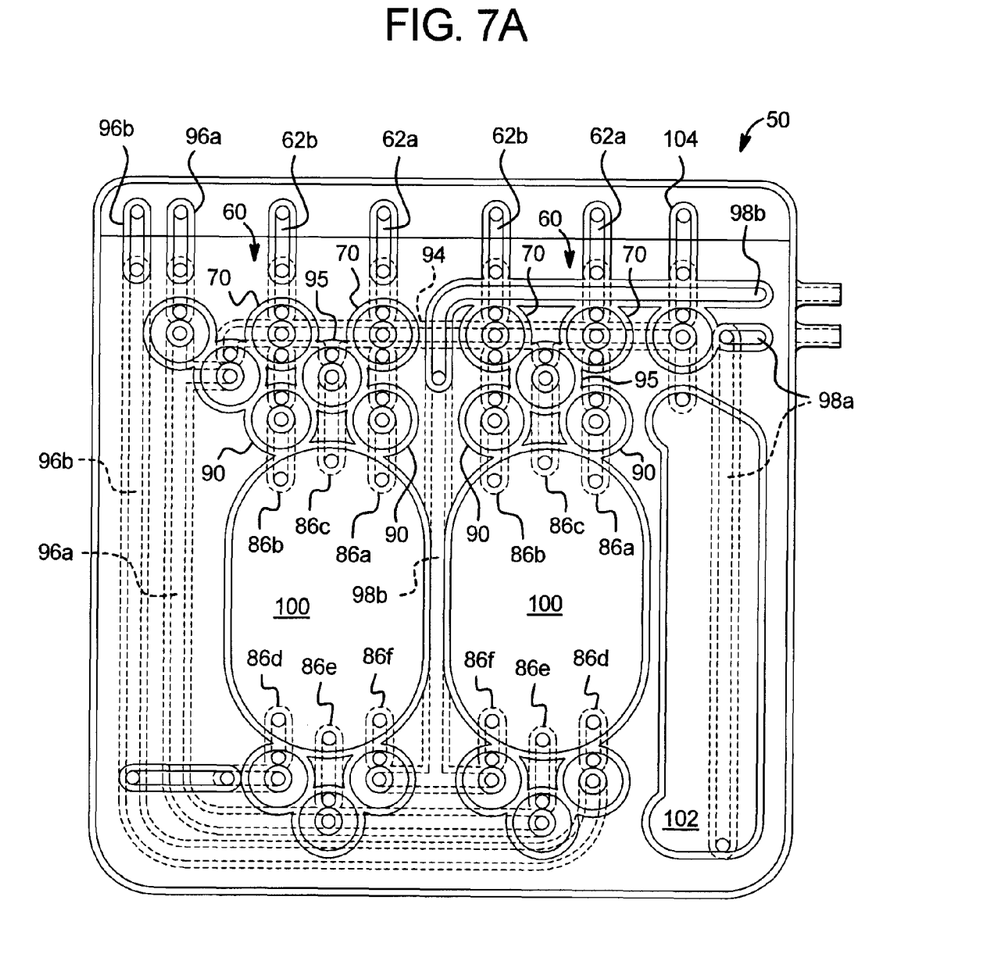
FIG. 7A is a side elevation view showing a pump chamber and valve chamber actuation side of a disposable cassette employing the valve arrangement of FIGS. 3 to 6.

In FIG. 6, flexible sheeting 58 is pulled away from first outlet 74 of valve chamber 70, while the flexible sheeting is pushed against outlet 74 of downstream valve chamber 90. This prevents fluid from flowing to pump pathway 84 and first pump chamber opening 86a, but allows fluid to flow from first outlet 74 of dual outlet valve chamber 70, through a manifold pathway 94, to an inlet 72 of intermediate valve 95, for example. Fluid can flow through valve 95, through pathway 92 and third pump opening 86c to pump chamber 100 as seen in FIGS. 3 and 7A. As also seen in FIGS. 7A and 8, manifold pathway 94 enables valve arrangement 60 to communicate with a second valve arrangement 60 operating with a second pump 100.

To shut off flow from both outlets 74 and 78 of dual outlet valve chamber 70, flexible sheeting 58 is pressed against ports 76 of both valve chambers 70 and 90. To allow flow from both outlets 74 and 78, flexible sheeting 58 is pulled away from ports 76 of both valve chambers 70 and 90.

Valve configuration 60 enables first and second medical fluids, such as, first and second dialysis fluid components (e.g., glucose and bicarbonate) to be pumped, selectively and proportionally, through any one, two or three of pump openings 86a to 86c. Configuration 60 for example enables a first fluid to be pumped from solution inlet pathway 62a, through pump chamber opening 86a, while a second fluid is pumped from solution inlet pathway 62b through the second and third pump chamber openings 86b and 86c. The configuration alternatively enables the first fluid to be pumped through first and third pump chamber openings 86a and 86c, while the second fluid is pumped through second pump chamber opening 86b. The configuration further alternatively enables the first fluid to be pumped through all three pump chamber openings 86a to 86c. The configuration still further alternatively enables the second fluid to be pumped through all three pump openings 86a to 86c.

Figure 8:
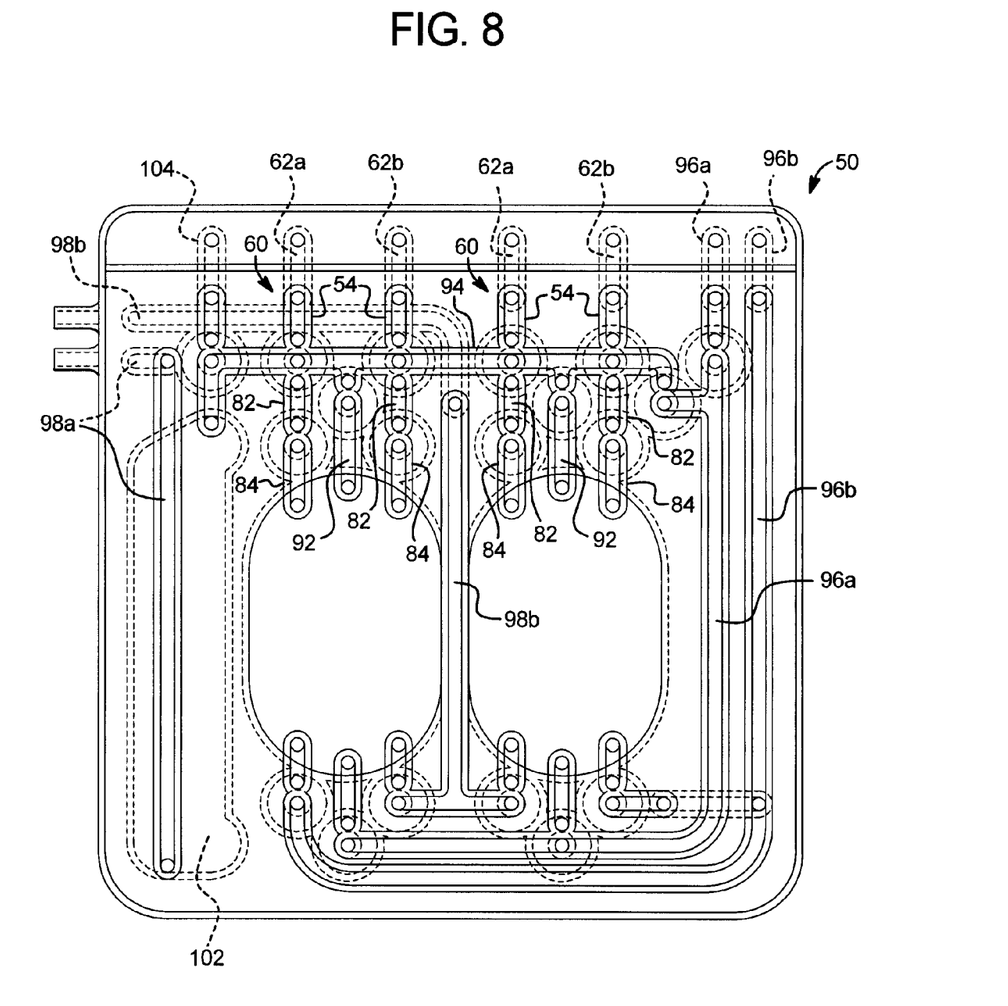
FIG. 8 is a flow path side of the disposable cassette of FIG. 7A.

Referring additionally to FIGS. 7A and 8, one embodiment for cassette 50 employing two valve arrangements 60 and two pump chambers 100 is illustrated. Besides solution inlet pathways 62a and 62b, cassette 50 includes to- and from-patient pathways 96a and 96b, respectively, a to-heater pathway 98a and a from-heater pathway 98b. To-heater pathway 98a leads to an air separation chamber 102. Cassette 50 also includes a drain pathway 104.

Pump chamber openings 86a to 86c can also be used as pump outlets on the pump-out stroke. Here, each opening can be used to deliver fluid to manifold line 94, which is in communication with to-patient pathway 96a. It is preferable from an arm handling standpoint however to pump out the bottom of pump chambers 100. To this end, to-patient pathway 96a also communicates fluidly with lower pump chamber opening 86e shown in FIG. 8. From-patient pathway 96b communicates with lower, outer pump chamber openings 86d shown in FIG. 8. Lower, inner pump chamber openings 86f in FIG. 8 communicate fluidly with to-heater line 98a.

Figure 7B:
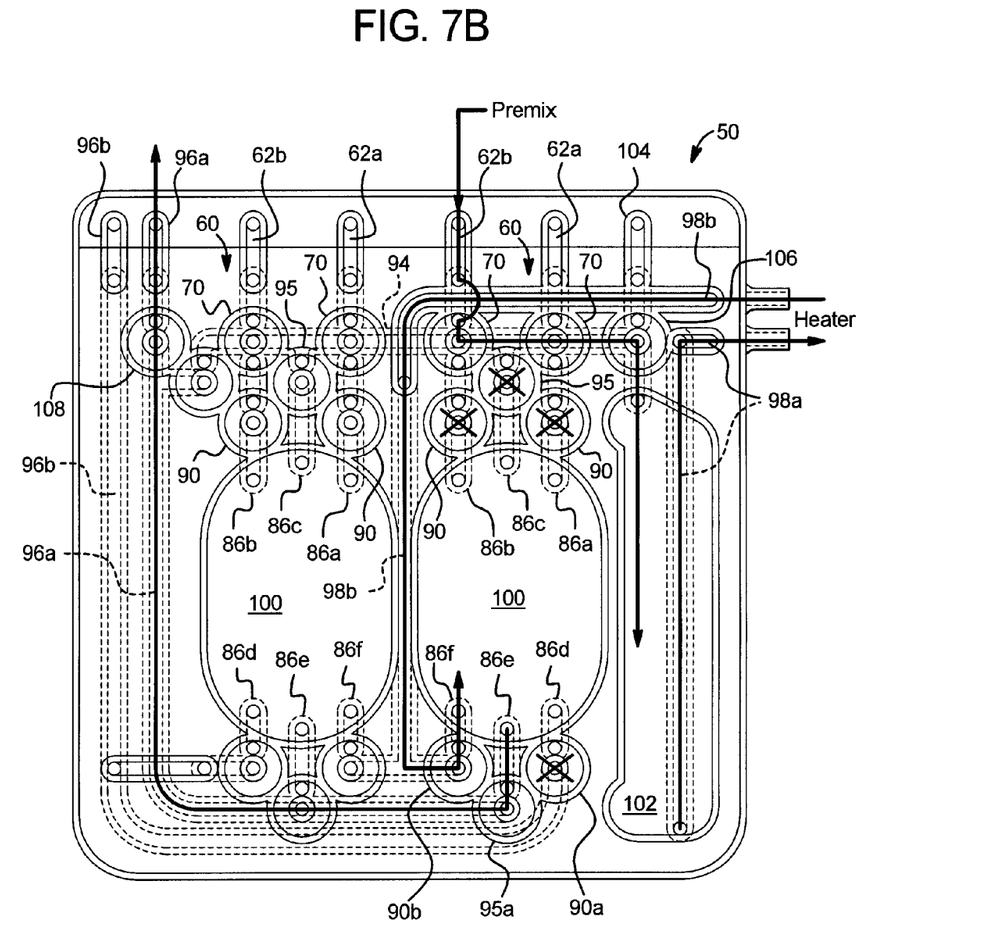
FIG. 7B illustrates one embodiment for a pump-to-patient pathway using the pass through valves of the present disclosure.

FIG. 7B illustrates one embodiment of a pump-to-patient flow path using a premixed dialysis fluid for right pump chamber 100. Here, the fluid is heated before being sent to the patient. The pathway illustrated is for both the pump-in and pump-out strokes. Valve chambers associated with right pump chamber 100 that are marked with an X are closed for both the pump-in and pump-out strokes. Associated valve chambers not marked with an X may be closed at some point during the pump-in and pump-out strokes.

During the pump-in stroke, premixed dialysis fluid enters cassette 50 through inlet fluid pathway 62b. Downstream valve chamber 90 inline with inlet fluid pathway 62b is closed, which also closes second outlet 78 of dual outlet valve chamber 70 inline with inlet fluid pathway 62b. First outlet 74 of dual outlet valve chamber 70 inline with inlet fluid pathway 62b is opened. Upper intermediate valve chamber 95 is closed. Downstream valve chamber 90 inline with inlet fluid pathway 62a is closed, which also closes second outlet 78 of dual outlet valve chamber 70 inline with inlet fluid pathway 62a. First outlet 74 of dual outlet valve chamber 70 inline with inlet fluid pathway 62a is opened. A to-heater valve chamber 106 is opened so fluid can enter air trap 102. Lower valve chambers 90a and 95a are closed, so no fluid flows in through pump chamber apertures 86d and 86e. Lower valve chamber 90b is opened so heated fluid returning from the heater can enter right pump chamber 100 through pump chamber aperture 86f.

During the pump-out stroke, lower intermediate single outlet valve chamber 95a is opened, while lower single outlet valve chambers 90a and 90b are closed, allowing fluid to leave right pump chamber 100 through pump chamber aperture 86e. Upper valve chambers 90 and 95 are all closed, so no fluid can flow out through pump chamber apertures 86a to 86c. A to-patient valve chamber 108 is opened allowing heated, premixed dialysis fluid to be pumped to the patient.

Referring also to FIGS. 3 to 6, dialysis fluid according to the flow path shown in FIG. 7B, is pumped from inlet 62b, through pathway 54, through first outlet 74, through underside pathway 94, through air trap 102, through to-heater pathway 98a, through the heater (not shown), through from-heater pathway 98b, through valve 90b, into the pump chamber through pump chamber opening 86f on the pump-in stroke, through right pump chamber 100, out pump chamber 100 through pump chamber opening 86e on the pump-out stroke, through lower intermediate valve 95, through to-patient pathway 96a and to-patient valve 108 to the patient. In FIG. 7B, left pump chamber 100 can be pumping premixed dialysis fluid out while right pump chamber is pumping the fluid in and vice versa.

Figure 7C:
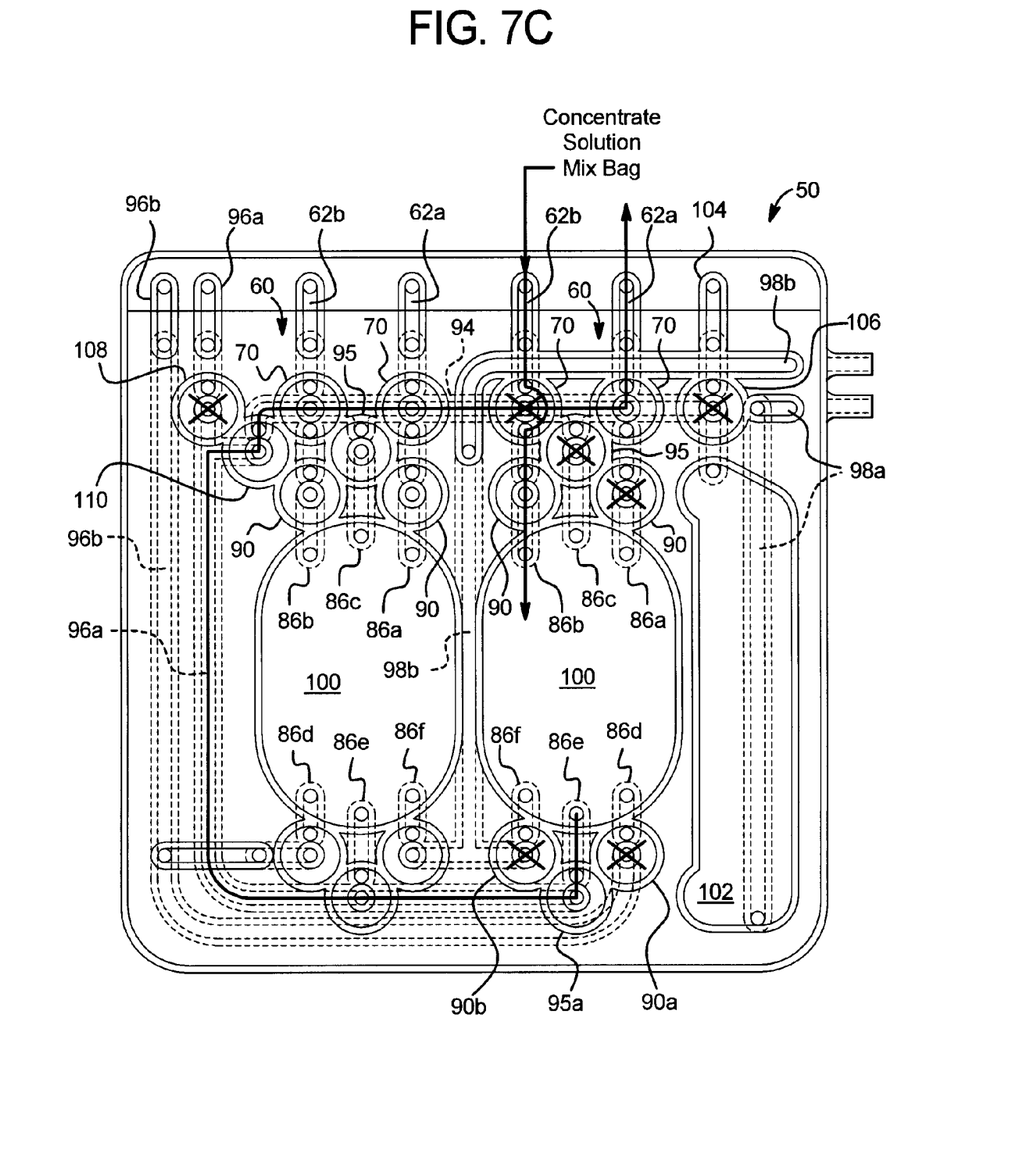
FIG. 7C illustrates another embodiment for a pump-to-patient pathway using the pass through valves of the present disclosure.

FIG. 7C illustrates one embodiment of a pump-to-mixer flow path for right pump chamber 100 when a concentrate solution is mixed with at least one other concentrate solution instead of using a premixed dialysis fluid. Here, the fluid is not heated before being sent to the mixer. Instead, the dialysis fluid is heated after it has been mixed. Not heating dialysis fluid until it has been mixed aids in mixing accuracy and prevents uneven heating of two or more concentrates. The pathway illustrated is for both the pump-in and pump-out strokes. Valve chambers associated with right pump chamber 100 that are marked with an X are closed for both the pump-in and pump-out strokes. Associated valve chambers not marked with an X may be closed at some point during the pump-in and pump-out strokes.

During the pump-in stroke, an unmixed dialysis concentrate enters cassette 50 through inlet fluid pathway 62b. Here, first outlet 74 of dual outlet valve chamber 70 inline with inlet fluid pathway 62b is closed, while downstream valve chamber 90 inline with inlet fluid pathway 62b is opened. Upper intermediate valve chamber 95 and downstream valve chamber 90 inline with inlet fluid pathway 62a are closed. Lower valve chambers 90a, 90b and 95 are all closed, so no fluid flows in through pump chamber apertures 86d to 86f.

During the pump-out stroke, upper valve chambers 90 and 95 are closed, which also closes second outlets 78 of upper dual outlet valve chambers 70, so no fluid flows out through pump chamber apertures 86a to 86c. First outlet 74 of upper dual outlet valve chamber 70 inline with inlet fluid pathway 62a is opened. Lower single outlet valve chambers 90a and 90b are closed, while lower intermediate valve chamber 95a is opened. To-heater valve chamber 106 is closed. To-patient valve chamber 108 is closed. A diverter valve chamber 110 is opened.

Referring also to FIGS. 3 to 6, dialysis fluid according to the flow path shown for FIG. 7C is pumped from inlet 62b, through pathway 54, around closed first outlet 74, through second outlet 78 of dual outlet valve chamber 70 inline with inlet 62b, through pathway 82, into downstream valve chamber 90, out outlet 74 of valve chamber 90, through pathway 84 and pump chamber aperture 86b into right pump chamber 100 on the pump-in stroke, out the pump chamber through pump chamber aperture 86e, through lower intermediate valve 95a, through to-patient pathway 96a, through diverter valve chamber 10, into dual outlet valve chamber 70 inline with inlet 62a, through first outlet 74, out of valve chamber 70 via inlet 72, out inlet 62a to the mixer or mixing bag.

Here, it should be appreciated that dual outlet valve chamber 70 inline with "inlet 62a" is operated in reverse of the way it has been described above, for example in connection with FIGS. 3 to 6. Here, "outlet 74" as described above is used as an inlet for the valve chamber and "inlet 72" as described above is used as an outlet for the valve chamber. Second outlet 78 is controlled again via downstream valve 90. However, second "outlet 78" could also be used as an inlet to dual outlet valve chamber 70, wherein fluid can exit through one or both of "inlet 72" and first outlet 74. It is also conceived that the same or different fluids can flow into any two apertures 72, 74 and 78 of valve chamber 70, and flow out of the remaining aperture 72, 74 and 78. Any aperture 72, 74 and 78 of valve chamber 70 can be used as an inlet or an outlet.

Online mixing can be performed in different ways. For example, both pump chambers 100 could be used to pump different concentrates to the mixing bag or container, wherein solution flows from the mixer, through the heater, to the patient. Left and right pump chambers 100 could be alternating or pumping-in and pumping-out at the same time. The mixer can be a bag formed as a portion of cassette 50 or either a section of tubing.

Alternatively, one pump chamber, e.g., right pump chamber 100 is pumping both concentrates, in turn, to the mixer, while the other pump chamber 100 pulls mixed fluid from the mixer and pumps the mixed fluid through the heater to the patient.

Figure 7D:
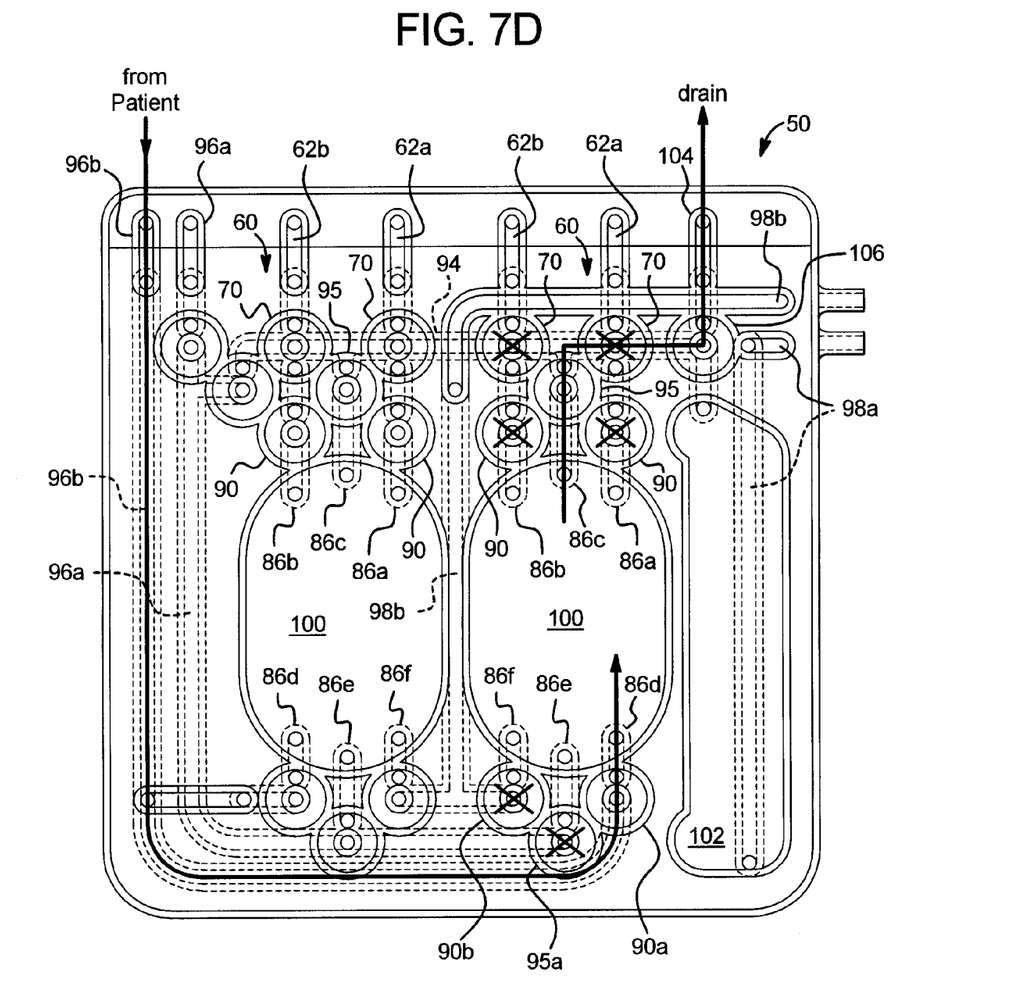
FIG. 7D illustrates one embodiment for patient-to-drain pathway using the pass through valves of the present disclosure.

FIG. 7D illustrates one embodiment of a pump-to-drain flow path for right pump chamber 100. The pathway illustrated is for both the pump-in and pump-out drain strokes. Valve chambers associated with right pump chamber 100 that are marked with an X are closed for both the pump-in and pump-out strokes. Associated valve chambers not marked with an X may be closed at some point during the pump-in and pump-out drain strokes.

During the pump-in drain stroke, effluent or spent dialysis fluid from the patient enters cassette 50 through a from-patient port and flow through from-patient line 96b. Lower valve chambers 90b and 95a are closed. Lower valve chamber 90a is opened allowing effluent dialysis fluid to enter right pump chamber 100 through aperture 86f. All three upper valves 90, 90 and 95 are closed, preventing fluid from being pumped into right pump chamber 100 through any of apertures 86a to 86c.

During the pump-out drain stroke, lower valve chambers 90a, 90b and 95a are closed, so no effluent fluid can flow out through pump chamber apertures 86d to 86f. Pump 100 pumps effluent out through intermediate valve chamber 95 (into port 74 and out inlet 72 of valve chamber 95) into manifold pathway 94 located on reverse side of cassette 50. Upper downstream valve chambers 90 are closed, intermediate valve 95 is opened. Both first outlets 74 of dual outlet valve chambers 70 are closed, forcing effluent to flow through pathway 94, into to-heater valve chamber 106, through "outlet 74" and out to-heater valve chamber 106, through "inlet 72", through drain port 104, and to a drain bag or house drain. Pump chambers 100 can alternate during the drain cycle to maintain a relatively continuous flow from and pressure to the patient.

While valve arrangement 60 includes a single outlet valve chamber 90 downstream from dual outlet valve chamber 70, an alternative arrangement can include a second dual outlet valve chamber 70 placed downstream from an upstream dual outlet valve chamber 70. Here, a single outlet valve chamber 90 can be located downstream from the second, downstream dual outlet valve chamber. A further alternative arrangement includes replacing intermediate single outlet valve chamber 95 with a dual outlet valve chamber 70 and placing a single outlet valve chamber 90 or 95 downstream from the dual outlet valve chamber 70 that replaces the intermediate chamber 95. It is envisioned to provide any desirable combination of series and/or parallel flow paths using any combination of dual outlet valve chambers 70 and single outlet valve chambers 90 or 95. In one embodiment, each flow path terminates with a single outlet valve chamber 90 or 95.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A disposable pumping cassette comprising:
a pump chamber;
a first flow path leading from the pump chamber to an outlet of a first valve chamber;
a second flow path leading from an inlet of the first valve chamber to a first outlet of a second valve chamber;
the second valve chamber further including an inlet and a second outlet;
a flexible sheet positioned to selectively open and close the outlet of the first valve chamber and the second outlet of the second valve chamber; and
a third fluid flow path extending from the second outlet of the second valve chamber, the third fluid flow path including at least one characteristic selected from the group consisting of: (i) leading to a third valve chamber; and (ii) being positioned at an angle of at least about forty-five degrees with respect to at least one of the first and second fluid flow paths.

2. The disposable pumping cassette of claim 1, which includes a base wall, and wherein at least one of the inlets of the first valve chamber, the inlet of the second valve chamber, and the first outlet of the second valve chamber includes an aperture in the base wall.

3. The disposable pumping cassette of claim 2, wherein at least one of the first outlet of the first valve chamber and the second outlet of the second valve chamber includes a port raised from the base wall.

4. The disposable pumping cassette of claim 3, wherein the port is raised on a first side of the base wall, at least one of the first and second flow paths residing on a second side of the base wall.

5. The disposable pumping cassette of claim 2, wherein at least one of the first and second valve chambers includes valve chamber walls extending from the base wall.

6. The disposable pumping cassette of claim 5, the flexible membrane sealed to at least one of the valve chamber wall and an outer wall connected to the base wall.

7. The disposable pumping cassette of claim 2, wherein at least one of the first and second flow paths includes path forming walls extending from the base wall.

8. The disposable pumping cassette of claim 7, the flexible sheet a first flexible sheet, and including a second flexible sheet sealed to the at least one path forming wall or to an outer wall connected to the base wall.

9. The disposable pumping cassette of claim 1, wherein the pump chamber, the first flowpath, the second flow path, the first valve chamber and the second valve chamber are formed as a rigid piece.

10. The disposable pumping cassette of claim 1, the third valve chamber including at least one characteristic selected from the group consisting of: (i) including first and second outlets and (ii) being in fluid communication with the pump chamber.

11. The disposable pumping cassette of claim 1, which includes a fourth fluid flow path extending from the inlet of the second valve chamber.

12. A disposable pumping cassette comprising:
a first valve chamber including an inlet and first and second outlets;
a second valve chamber including an inlet and an outlet, the second valve chamber openable to allow dialysis fluid to flow through one of the first and second outlets of the first valve chamber, through the outlet of the second valve chamber; and
wherein the second valve chamber is closeable to allow the dialysis fluid to flow through one of the first and second outlets of the first valve chamber to a third valve chamber.

13. The disposable pumping cassette of claim 12, wherein the outlet of the second valve chamber is closeable to allow the dialysis fluid to be diverted from one of the first and second outlets of the first valve chamber, away from the second valve chamber.

14. The disposable pumping cassette of claim 12, wherein an outlet of the second valve chamber is openable to allow dialysis fluid to flow through one of the first and second outlets of the first valve chamber, through the outlet of the second valve chamber.

15. The disposable pumping cassette of claim 12, wherein one of the first and second outlets of the first valve chamber is openable and closeable, while the other of the first and second outlets is not.

16. The disposable pumping cassette of claim 12, which includes a flexible sheet configured to open and close one of the first and second outlets of the first valve chamber and the outlet of the second valve chamber.

17. The disposable pumping cassette of claim 12, which includes a pump chamber in operable communication with at least one of the first and second valve chambers.

18. The disposable pumping cassette of claim 12, operable with a dialysis instrument, the instrument and cassette configurable such that any of the inlets and outlets of either the first and second valve chambers is operated interchangeably as a valve inlet or a valve outlet.

19. A disposable pumping cassette comprising:
a pump chamber;
a first flow path leading from the pump chamber to an outlet of a first valve chamber;
a second flow path leading from an inlet of the first valve chamber to a first outlet of a second valve chamber;
the second valve chamber further including an inlet and a second outlet;
a flexible sheet positioned to selectively open and close the outlet of the first valve chamber and the second outlet of the second valve chamber; and
a third fluid flow path extending from the second outlet of the second pump valve chamber, the third fluid flow path leading to a third valve chamber.

20. A disposable pumping cassette comprising:
a pump chamber;
a first flow path leading from the pump chamber to an outlet of a first valve chamber;
a second flow path leading from an inlet of the first valve chamber to a first outlet of a second valve chamber;
the second valve chamber further including an inlet and a second outlet;
a flexible sheet positioned to selectively open and close the outlet of the first valve chamber and the second outlet of the second valve chamber; and
a third fluid flow path extending from the inlet of the second valve chamber.

* * * * *